United States Patent
Seok et al.

(10) Patent No.: US 9,829,449 B2
(45) Date of Patent: Nov. 28, 2017

(54) METHOD AND APPARATUS FOR TESTING PERFORMANCE OF THERMAL BARRIER COATING LAYER

(71) Applicant: Research & Business Foundation SUNGKYUNKWAN UNIVERSITY, Suwon-si (KR)

(72) Inventors: Changsung Seok, Gwacheon-si (KR); Yongseok Kim, Incheon (KR)

(73) Assignee: Research & Business Foundation Sungkyunkwan University, Sunwon-si (KR)

(*) Notice: Subject to any disclaimer, the term of this patent is extended or adjusted under 35 U.S.C. 154(b) by 706 days.

(21) Appl. No.: 14/337,555

(22) Filed: Jul. 22, 2014

(65) Prior Publication Data

US 2014/0369378 A1 Dec. 18, 2014

Related U.S. Application Data (63) Continuation of application No. PCT/KR2013/000745, filed on Jan. 30, 2013.

(30) Foreign Application Priority Data

Jan. 31, 2012 (KR) .................. 10-2012-0009535

(51) Int. Cl.
  *G01K 3/14* (2006.01)
  *G01N 25/18* (2006.01)
(52) U.S. Cl.
  CPC .................. *G01N 25/18* (2013.01)
(58) Field of Classification Search
  CPC  G01K 3/14; G01K 3/00; G01K 17/00; G01K 17/08; G01N 25/18; G01N 25/00; G01N 25/20; G01N 25/72

(Continued)

(56) References Cited

U.S. PATENT DOCUMENTS 4,553,852 A * 11/1985 Derderian .............. G01K 17/20
  374/1
4,630,938 A * 12/1986 Piorkowska-
  Palczewska ........... G01N 25/18
  374/29

(Continued)

FOREIGN PATENT DOCUMENTS

JP  7-280715 A  10/1995
JP  2010-8403 A  1/2010

(Continued)

OTHER PUBLICATIONS

Korean Office Action issued on Aug. 14, 2013 in counterpart Korean Application No. 10-2012-0009535 (5 Pages, in Korean).

(Continued)

*Primary Examiner* — Gail Kaplan Verbitsky
(74) *Attorney, Agent, or Firm* — NSIP Law (57) ABSTRACT

A method and an apparatus for testing thermal performance of a coating layer are provided. The method for testing thermal performance of a coating layer involves obtaining a first thermal gradient by exposing one side of a metal base test piece to heat and exposing another side of the metal base test piece to a cooling air; obtaining a second thermal gradient by exposing a coating layer side of a coating layer test piece to heat and exposing an opposite side to a cooling air; calculating an exterior temperature $T_f$ of a coating layer of the coating layer test piece and a temperature $T_e$ of a boundary side of the coating layer using the first thermal gradient; and calculating a temperature difference $T_\Delta$ between the exterior temperature $T_f$ of the coating layer and the temperature $T_e$ of the boundary side of the coating layer.

10 Claims, 4 Drawing Sheets

(58) Field of Classification Search
USPC ..... 374/29, 30, 137, 166, 44, 4, 5, 111, 112, 374/57
See application file for complete search history.

(56) References Cited

U.S. PATENT DOCUMENTS

| | | | | |
|---|---|---|---|---|
| 4,812,050 | A * | 3/1989 | Epstein | G01K 17/20 250/252.1 |
| 4,840,495 | A * | 6/1989 | Bonnefoy | G01N 25/18 374/43 |
| 5,582,485 | A * | 12/1996 | Lesniak | G01N 25/72 250/330 |
| 5,800,152 | A * | 9/1998 | Taimatu | C22C 38/14 420/40 |
| 6,116,777 | A * | 9/2000 | Pause | G01N 25/18 374/43 |
| 6,398,503 | B1 * | 6/2002 | Takahashi | F16L 59/00 416/241 B |
| 6,408,256 | B1 * | 6/2002 | Hittle | G01K 17/20 374/179 |
| 7,004,622 | B2 * | 2/2006 | Hardwicke | G01K 1/14 374/141 |
| 7,409,113 | B2 * | 8/2008 | Sumi | B82Y 20/00 385/14 |
| 7,655,326 | B2 * | 2/2010 | Torigoe | C23C 4/18 416/241 B |
| 7,748,197 | B2 * | 7/2010 | Romes | G01K 17/08 374/135 |
| 8,128,278 | B2 * | 3/2012 | Gotkis | G01B 21/085 374/110 |
| 8,616,764 | B2 * | 12/2013 | Ladru | C23C 4/02 374/1 |
| 8,759,770 | B1 * | 6/2014 | Woods | G01N 25/72 250/330 |
| 2004/0156724 | A1 * | 8/2004 | Torigoe | C23C 4/18 416/241 R |
| 2006/0256834 | A1 * | 11/2006 | Chang | F28D 15/00 374/5 |
| 2007/0223560 | A1 * | 9/2007 | Boese | C23C 4/18 374/141 |
| 2011/0142091 | A1 * | 6/2011 | Wardle | B82Y 15/00 374/45 |
| 2012/0294329 | A1 * | 11/2012 | Miller | G01N 25/18 374/44 |
| 2013/0163634 | A1 * | 6/2013 | Smith | G01N 3/42 374/45 |
| 2014/0010258 | A1 * | 1/2014 | Hyun | G01N 25/18 374/44 |

FOREIGN PATENT DOCUMENTS

| | | |
|---|---|---|
| KR | 10-2007-0024060 A | 3/2007 |
| KR | 10-2011-0080522 A | 7/2011 |

OTHER PUBLICATIONS

Kim, I. H., et al. "Thermal Fatigue Test of Thermal Barrier Coating by Real Temperature Gradient" International Journal of Precision Engineering and Manufacturing, Journal of 2010 Spring Conference, 2010. pp. (3 pages, in Korean, with partial English translation).

International Search Report issued May 14, 2013 in counterpart International Application No. PCT/KR2013/000745 (4 pages, in Korean, with English translation).

* cited by examiner

METHOD AND APPARATUS FOR TESTING PERFORMANCE OF THERMAL BARRIER COATING LAYER

CROSS-REFERENCE TO RELATED APPLICATIONS

This application is a continuation application of International Application No. PCT/KR2013/000745 filed Jan. 30, 2013, claiming priority based on Korean Patent Application No. 10-2012-0009535 filed Jan. 31, 2012, the entire disclosure of all of which are incorporated herein by reference for all purposes.

BACKGROUND

1. Field

The following description relates to a method and an apparatus for testing thermal insulation performance of a heat shield coating layer, and to a method and an apparatus for evaluating heat-shielding performance of a coating layer formed on a gas turbine component using cooling air and a high temperature electric furnace.

2. Description of Related Art

One of core components of a gas turbine is the blades. The blades operate under a high-temperature and high-pressure condition. For example, depending on the gas turbine, the blades may be exposed to an environment having a temperature that reaches 200° C., 600° C., or even 900° C. Thus, the blades are subjected to an environment that may easily cause corrosion and oxidation. Further, the blades are subject to a strong centrifugal force due to the high-speed rotation of the blades. Accordingly, the blades are subjected to a high degree of mechanical fatigue. In order to protect the mechanical integrity of the blades and to protect the blades from its high temperature and high pressure environments while maintaining durability, a heat shield coating layer made of a ceramic material is formed around the blade to reinforce its heat shield performance. However, the heat shield coating layer applied to a surface of the blade may also be subject to thermal and mechanical fatigue. Therefore, in order to obtain reliability of a blade of a gas turbine, it is necessary to evaluate the performance of the blade that includes a heat shield coating layer.

Techniques used to evaluate the performance of a heat shield coating layer of a gas turbine component includes a method of testing a blade to which a thermal shield coating has been actually applied. But it is difficult to measure and evaluate the performance of the blade due to high material cost and complicated shape of the blade. Therefore, a method of evaluating the performance of a heat shield coating layer of a blade is generally performed on a test piece extracted from the blade.

Such a method of evaluating the heat shield performance is generally conducted by simply measuring the heat conductivity, which requires a test piece of a far more exaggerated thickness than the thickness of a ceramic coating layer that is actually applied. Thus, there exists much difficulty in manufacturing a test piece.

However, as it is not accurate to regard a test piece having an exaggerated thickness as an accurate duplication of a heat shield coating layer under an actual conduction, the reliability of measurement may be reduced by using the test piece.

Furthermore, an existing test method cannot evaluate the effects of a bond coating layer that is applied to the blade to combine the metal surface of the test piece with a ceramic coating layer or evaluate the effects resulting from the complicated shapes of various layers and the interfaces between the layers.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method for testing thermal performance of a coating layer includes obtaining a first thermal gradient by exposing one side of a metal base test piece to heat and exposing another side of the metal base test piece to a cooling air, obtaining a second thermal gradient by exposing a coating layer side of a coating layer test piece to heat and exposing an opposite side to a cooling air, calculating an exterior temperature $T_f$ of a coating layer of the coating layer test piece and a temperature $T_e$ of a boundary side of the coating layer using the first thermal gradient, and calculating a temperature difference $T_\Delta$ between the exterior temperature $T_f$ of the coating layer and the temperature $T_e$ of the boundary side of the coating layer.

The method may further involve evaluating thermal performance of the coating layer based on the calculated temperature difference $T_\Delta$ between the exterior temperature $T_f$ of the coating layer and the temperature $T_e$ of the boundary side of the coating layer.

The method may further involve, after the obtaining of the first thermal gradient, performing a first surface temperature calculating step of calculating a surface temperature of both sides of the test piece of the metal base using the obtained first thermal gradient, and performing a convective heat transfer coefficient calculating step of calculating a convective heat transfer coefficient of an interior of a furnace producing the heat and the cooling air using surface temperatures of both sides of the test piece of the metal base, and performing a second surface temperature calculating step of calculating a surface temperature of both sides of the test piece of the metal layer using the obtained second thermal gradient. The calculating of the exterior temperature $T_f$ may involve calculating the exterior temperature $T_f$ of the coating layer and the temperature $T_e$ of the boundary side of the coating layer using the convective heat transfer coefficient and the surface temperatures of both sides of a metal layer of the coating layer test piece or the metal base test piece.

The obtaining of the first thermal gradient may involve measuring an internal temperature at different locations along a thickness direction of the metal base test piece, and the obtaining of the second thermal gradient may involve measuring an internal temperature at different locations along a thickness direction of a metal layer of the coating layer test piece.

The obtaining of the first thermal gradient may involve measuring an internal temperature at different locations along a thickness direction of the metal base test piece, and the obtaining of the second thermal gradient may involve measuring an internal temperature at different locations along a thickness direction of a metal layer of the coating layer test piece.

The first thermal gradient or the second thermal gradient representing an internal temperature along a thickness direction of the metal base test piece or the coating layer test piece may be determined by using the following formula: $T=aX+b$, in which T represents a temperature along the thickness direction of the metal base test piece or the coating layer test piece; X represents coordinates along the thickness direction of the metal base test piece or the coating layer test piece; and a and b each represent a numerical value.

The first temperature gradient or the second temperature gradient representing an internal temperature along a thickness direction of the metal base test piece or the coating layer test piece may be determined by using the following formula: T=aX+b, wherein T represents a temperature along the thickness direction of the metal base test piece or the coating layer test piece; X represents coordinates along the thickness direction of the metal base test piece or the coating layer test piece; and a and b each represent a numerical value.

The metal base test piece may include a metal base having a shape of a coin, and the coating layer test piece comprises a second metal base having a shape of a coin and a ceramic coating layer disposed on one surface of the second metal base.

In another general aspect, there is provided a non-transitory computer readable recording medium storing an instruction that causes a computer to perform the method described above.

In yet another general aspect, there is provided an apparatus for evaluating thermal performance of a coating layer, the apparatus including a processor configured to: determine a first thermal gradient of a metal-base test piece in response to receiving a temperature measurement taken while one side of the metal-base test piece is exposed to heat and another side of the metal-base test piece is exposed to a cooling air; determine a second thermal gradient of a coating-layer test piece in response to receiving a temperature measurement taken while a coating layer side of the coating-layer test piece is exposed to heat and an opposite side of the coating layer test piece is exposed to a cooling air; and calculate an exterior temperature $T_f$ of a coating layer in the coating layer test piece and a temperature $T_e$ of a boundary side of the coating layer using the first thermal gradient.

The processor may be configured to calculate a temperature difference $T_A$ between the exterior temperature $T_f$ of the coating layer and the temperature $T_e$ of the boundary side of the coating layer.

The general aspect of the apparatus may include a temperature measuring device configured to measure a temperature on surfaces of the metal base test piece and the coating layer test piece.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

A general method for evaluating performance of a heat shield coating layer is to measure the heat conductivity of a test piece having a greater thickness than the thickness of a ceramic coating layer that is actually applied to a blade. The method involves burdensome production of the test piece. Further, it is difficult to duplicate the actual testing condition or to evaluate the effects of a bond coating layer that is applied to combine the metal surface of a blade with a ceramic coating layer or the effects of having interfaces of different shapes within the layers.

Thus, to improve the accuracy of the testing method, the difference of temperatures of both surfaces of a coating layer may be calculated or determined based on the thermal gradient of a metal base test piece, the convective heat transfer coefficient of a high temperature electrical furnace and cooling air, and the thermal gradient of a test piece of a coating layer. The difference of temperatures of both surfaces of a coating layer may be used to evaluate the heat shield performance of a coating layer with a greater accuracy.

In a general aspect, there is provided a method of testing the heat shield performance of a heat shield coating layer formed on a component of a gas turbine that operates under a high-temperature and hot-pressure environment.

Figure 1:
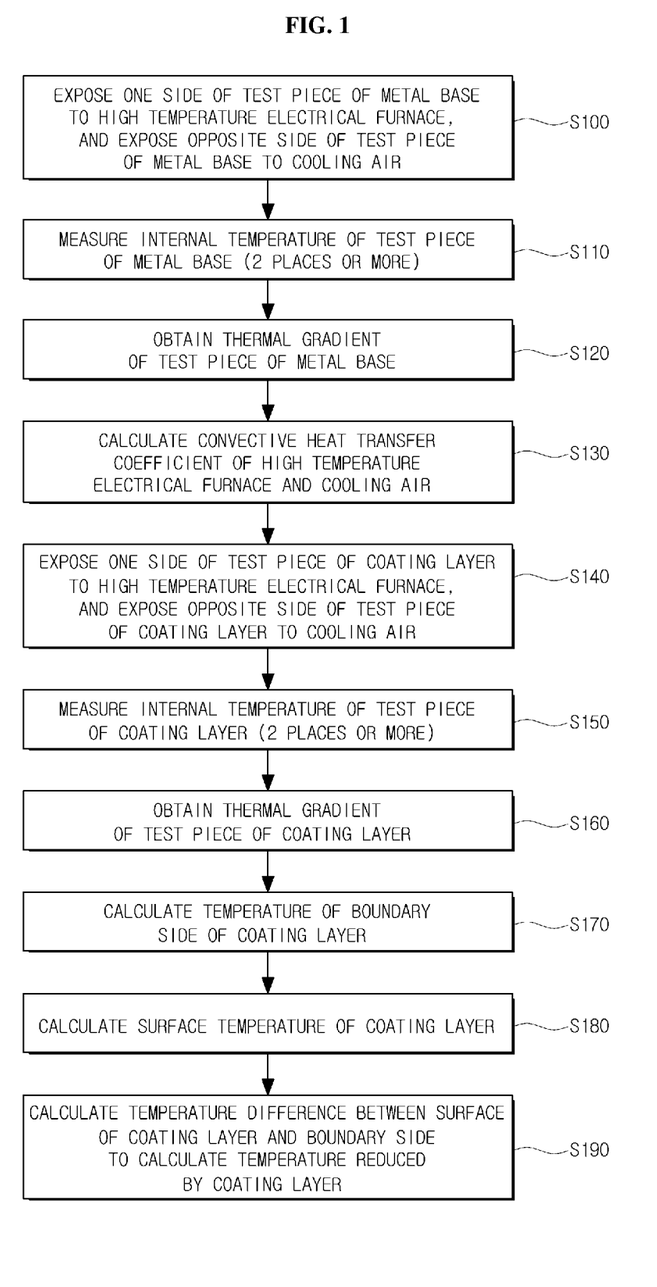
FIG. 1 is a flowchart illustrating an example of a method of testing thermal performance of a heat shield coating layer.
Figure 2A:
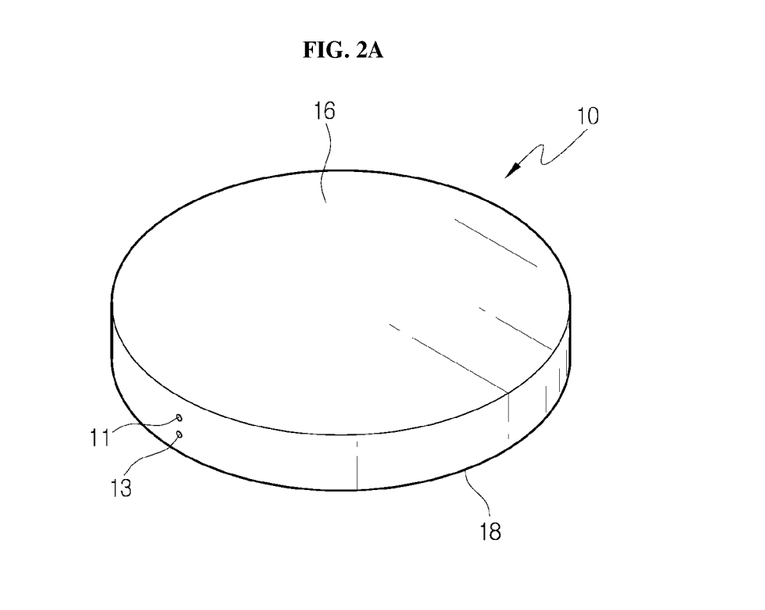
FIG. 2A is a perspective view of a test piece of a metal base that may be used in an example of a method of testing thermal performance of a heat shield coating layer.
Figure 2B:
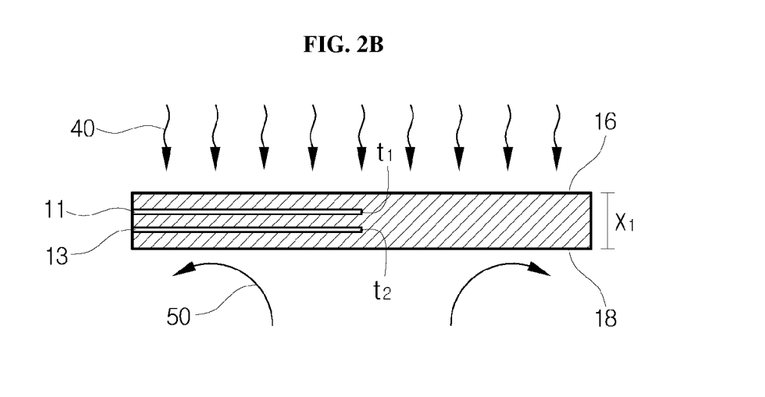
FIG. 2B is a cross-sectional view of a test piece of a metal base that may be used in an example of a method of testing thermal performance of a heat shield coating layer.
Figure 3A:
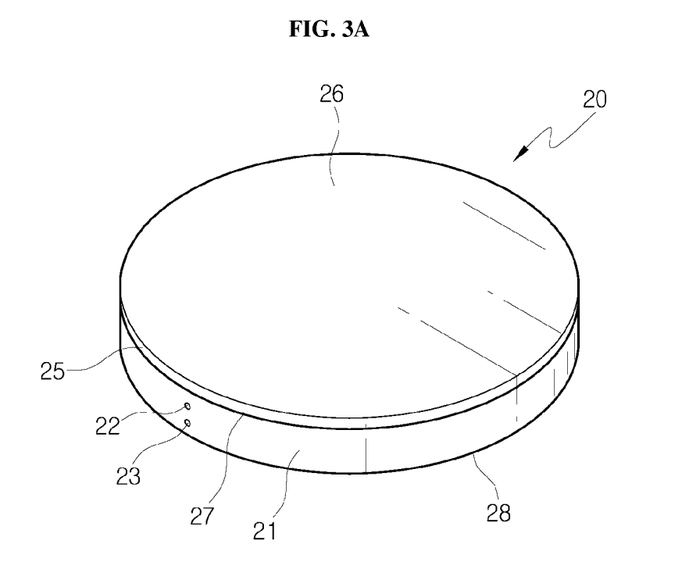
FIG. 3A is a perspective view of a test piece of a coating layer that may be used in another example of a method of testing thermal performance of a heat shield coating layer.
Figure 3B:
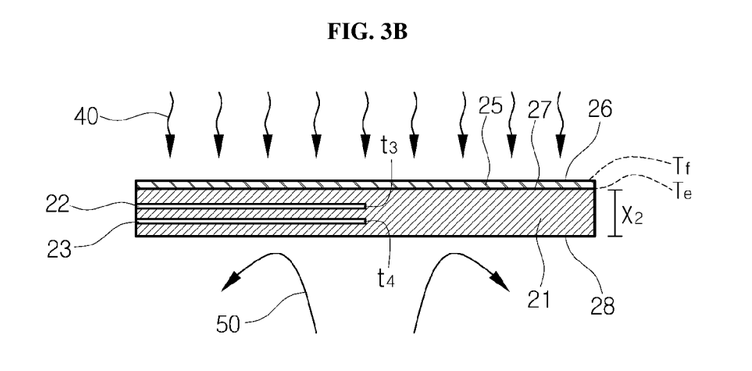
FIG. 3B is a cross-sectional view of a test piece of a coating layer that may be used in an example of a method of testing thermal performance of a heat shield coating layer.

FIG. 1 is a flowchart illustrating an example of a method of testing the performance of a heat shield coating layer. FIGS. 2A and 2B illustrate a perspective view and a cross-sectional view of a test piece of a metal base that may be used in an example of a method of testing the performance of a heat shield coating layer. FIGS. 3A and 3B illustrate a perspective view and a cross-sectional view of a test piece of a coating layer used in another example of a method of testing the performance of a heat shield coating layer.

The present disclosure provides a method for testing the heat-shielding performance of a heat shield coating layer that is applied to a metal component, such as a turbine blade, that operates under a high-temperature and high-pressure environment. For example, a method for obtaining a temperature difference between both sides of a coating surface through a thermal gradient occurring throughout the thickness of a coin-type test piece may involve heating one side of the coin-type test piece while cooling the opposite side of the coin-type test piece. The difference of temperature between both sides of the coating layer may be regarded as a temperature drop effect, in which the temperature drop and the heat shield performance may be regarded as being proportionate to each other.

First, a test piece 10 of a metal base is prepared. The test piece 10 of a metal base may have a shape of a coin, as illustrated in FIG. 2. The test piece is made of a same metal material as a blade of a gas turbine, and the test piece has two holes 11, 13 to which a temperature measuring device may be inserted up to the center of the test piece 10. The two holes are a first hole 11 and a second hole 13 that are spaced by a predetermined distance in the thickness direction of the test piece 10 of the metal base.

Referring to FIG. 1, in S100, the one side of the test piece 10 of the metal base is exposed to a high temperature electrical furnace 40, while the opposite side is exposed to cooling air 50, so as to duplicate the high-temperature and high-pressure environment of a gas turbine and the cooling effect produced by a cooling air 50. Herein, a temperature measuring device is inserted into the test piece 10 of the metal base through the processed first hole 11 and the second hole 13, to measure temperatures $t_1$, $t_2$ in the center of the test piece 10. A heating side 16 of the test piece 10 of the metal base is the side that is exposed to the high-temperature electrical furnace, and a cooling side 18 is the side that is exposed to the cooling air 50.

Using the internal temperatures $t_1$, $t_2$ of the test piece 10 of the metal base measured in step S110, a linear functional thermal gradient ($T_1$) formula that corresponds to the thickness $X_1$ of the test piece 10 of the metal base is used to determine a linear functional thermal gradient ($T_1$) in S120. The linear functional thermal gradient ($T_1$) formula is represented by Formula 1 below.

$$T_1 = a_1 X_1 + b_1 \quad \text{[Formula 1]}$$

In this example, the thermal gradient of the thickness direction inside the aforementioned test piece 10 of the metal base is based on the first linear function. However, in another example according to the present disclosure, the temperature of the test piece 10 of the metal base may be calculated by measuring a thermal gradient of a linear functional format in each of divided sections, and based on a formula in which dominant formulas of the thermal gradient of each section are mutually connected to one another.

Furthermore, the aforementioned thermal gradient formula of the test piece 10 of the metal base is not limited to the aforementioned, but may be measured and calculated in various ways considering the number of temperature data measured and measurement locations and so forth, thereby improving the reliability of the thermal gradient obtained.

In Formula 1, $X_1$ is substituted for 0, and the thickness value of the test piece of the metal base is substituted for $X_1$, respectively, to calculate the temperatures of both sides of the test piece 10 of the metal base, which correspond to the temperature of the heating side 16 and the temperature of the cooling side 18.

Then, based on the calculated temperature of the heating side 16 and the temperature of the air inside the high temperature electrical furnace 40, a convective heat transfer coefficient between the air inside the high temperature electrical furnace 40 and the surface of the test piece 10 of the metal base is calculated. Likewise, based on the calculated temperature of the cooling side 18 and the temperature of the cooling air 50, a convective heat transfer coefficient between the cooling air 50 and the surface of the test piece 10 of the metal base is calculated in S130.

Then, a test piece 20 of a coating layer is prepared. The test piece 20 of the coating layer may have a coin shape. The test piece 20 of the coating layer is manufactured by forming a coating layer 25 for improving heat shield performance on a metal base 21 such as a blade of the gas turbine. Inside the test piece 20 of the coating layer, a first hole 22 and a second hole 23 to which the temperature measuring device is to be inserted is formed in the thickness direction of the test piece 20 of the coating layer parallel to the top surface of the test piece 20 such that the first hole 22 and the second hole 22 are spaced from each other.

One side of the test piece 10 of the coating layer prepared as aforementioned is exposed to the high temperature electrical furnace 40, while the opposite side is exposed to cooling air 50 so as to copy the high temperature and high pressure environment as the gas turbine and cooling effect by the cooling air 50. Herein, the temperature measuring device is inserted into the first hole 22 and the second hole 23, and temperatures $t_3$, $t_4$ are measured, respectively, in S150. An exterior side of the coating layer 26 is the side that is exposed to the high temperature electrical furnace 40, and a boundary side 27 is the side that the coating layer 25 and the metal base 21 meet each other. Herein, the boundary side 27 can be regarded as an internal side of the coating layer 25. Furthermore, a cooling side 28 is the side that is exposed to the cooling air 50.

Using the internal temperatures $t_3$, $t_4$ of the test piece 20 of the coating layer measured at step S150, just as Formula 1, a linear functional thermal gradient $T_2$ formula according to the thickness $X_2$ of the test piece 20 of the coating layer is completed in S160.

$$T_2 = a_2 X_2 + b_2 \quad \text{[Formula 2]}$$

Furthermore, in S170, by substituting $X_2$ for 0 in math formula 2, a temperature value $T_e$ of the boundary side 27 is calculated. The temperature value $T_e$ of the boundary side 27 calculated herein may be regarded as the internal temperature of the coating layer 25.

Then, a temperature $T_f$ of the exterior side of the coating layer 26 is calculated using the convective heat transfer coefficient of the high temperature electrical furnace 40 calculated in step S130 and the internal temperature of the coating layer 25 calculated in step S170, that is the temperature value Te of the boundary side 27 in S180.

That is, it is possible to predict and calculated a temperature $T_f$ of the exterior side 26 of the coating layer 25 using the calculated convective heat transfer coefficient inside the high temperature electrical furnace, air temperature inside the high temperature electrical furnace, and the temperature $T_e$ of the boundary side 27.

Lastly, the difference between the temperature of the exterior side 26 of the coating layer $T_f$ and the internal temperature corresponds to the temperature difference ($T_A = T_f - T_e$) of the exterior side of the coating layer 26 and the boundary side 27. When the difference between the temperature of the exterior side 26 of the coating layer $T_f$ and the internal temperature is obtained, it is possible to obtain the temperature difference between both sides of the coating layer 25. That is, it becomes possible to obtain the temperature reduced by the coating layer 25 quantitatively, as in S190. Furthermore, based on the temperature reduced by the coating layer 25 obtained as aforementioned, it is possible to evaluate the heat shield performance by the coating layer 25.

In this example, the greater the difference between the finally obtained temperature $T_f$ of the exterior side 26 of the coating layer and the temperature $T_e$ between the coating layer and the metal base 21, the more the heat generated from the high temperature electrical furnace 40 is shielded by the test piece 20 of the coating layer. Thus, the heat is prevented from moving towards the metal base 21. Using this fact, it is possible to evaluate the performance of the coating layer in shielding heat.

Figure 4:
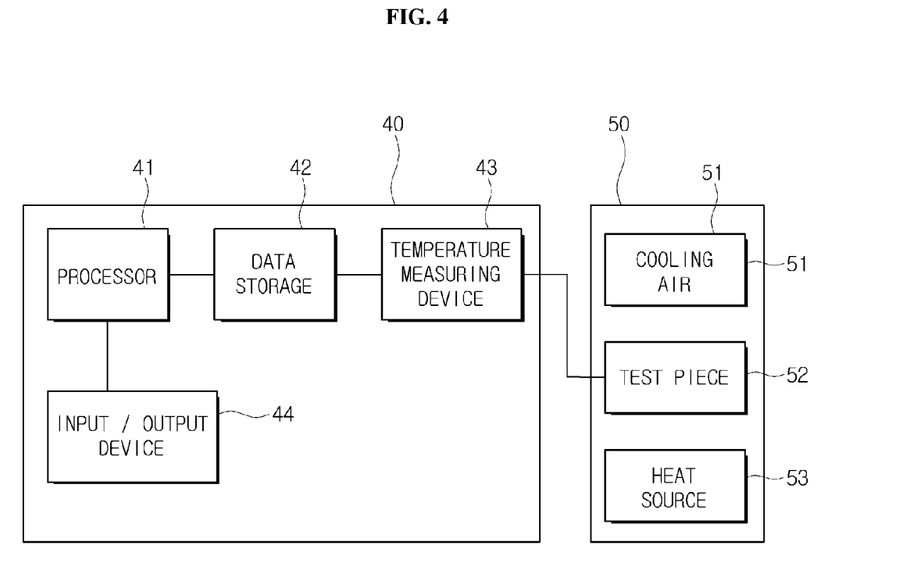
FIG. 4 is a schematic diagram illustrating an example of an apparatus for evaluating thermal performance of a heal shield coating layer.

FIG. 4 illustrates an example of an apparatus of testing thermal performance of a coating layer. The descriptions provided with references to FIGS. 1-3B applies to the apparatus illustrated in FIG. 4; thus, repetitive descriptions are omitted for conciseness.

Referring to FIG. 4, an apparatus 40 includes a processor 41, a data storage 42, a temperature measuring device 43, and an input/output device 44. The temperature measuring device 43 is configured to measure temperature of a test piece 53 located within a testing chamber 50. For example, the temperature measuring device 43 may include a probe. The testing chamber 50 may include a cooling air 51 or an opening or passage that allows access to a cooling air 51, and a heat source 53 such as a furnace. The temperature measurement taken by the temperature measuring device 43 may be received by the processor 41 via a data storage 42. The processor 41 may determine the thermal gradient of a test piece based on the temperature measurement to evaluate the thermal performance of a coating layer provided on a test piece 52.

In general, a method of evaluating the heat-shielding performance of a coating layer using a conventional test piece involves a burdensome process of manufacturing a test piece and a low reliability of results as the evaluation involves simply measuring the heat conduction of a test piece that does not fully reflect the actual operating condition. However, according to an example of a method of testing the thermal performance of a heat shield coating layer according to the present disclosure, measurements are taken under the same extreme conditions as the environment in which coating layers are actually used. Thus, it is possible to obtain a more reliable evaluation result.

Furthermore, because the heat shield performance is evaluated based on a method of comparing measurements using a test piece that has a coating layer and a test piece from which a coating layer has been removed, evaluations can be made by an easy and simple process.

According to another example, a method of testing the heat shield performance of a heat shield coating layer formed on a component of a gas turbine that operates under a high-temperature and hot-pressure environment is provided. The method may involve a first step of obtaining a thermal gradient in a thickness direction by exposing one side of a metal base test piece to high temperature electricity and exposing the other side of the metal base test piece to cooling air; a second step of obtaining a thermal gradient in a thickness direction by exposing a coating layer side of a test piece of a test piece of a coating layer to high temperature electricity and exposing the opposite side to cooling air; a third step of calculating an exterior temperature $T_f$ of the coating layer and a temperature Te of a boundary side of the coating layer using the thermal gradient of the metal base test piece obtained at the first step; and a fourth step of evaluating the thermal performance of the coating layer using a temperature difference $(T_A=T_f-T_e)$ between the exterior temperature $T_f$ of the coating layer and temperature Te of the boundary side of the coating layer.

The method may further include, after the first step, a first surface temperature calculating step of calculating a surface temperature of both sides of the metal base test piece using the thermal gradient of the metal base test specimen obtained at the first step after the first step; and a convective heat transfer coefficient calculating step of calculating a convective heat transfer coefficient of inside of the high temperature electrical furnace and the cooling air using surface temperatures of both sides of the metal base test piece, and a second surface temperature calculating step of calculating a surface temperature of both sides of the metal base test piece of the metal layer using the thermal gradient of the test piece of the metal layer obtained after the second step, wherein the third step may involve calculating an exterior temperature $T_f$ of the coating layer and a temperature $T_e$ of the boundary side of the coating layer using the convective heat transfer coefficient and the surface temperatures of both sides of the test piece of the metal layer.

The first step may involve obtaining a first thermal gradient formula by measuring an internal temperature at different locations along the thickness direction of the metal base test piece, and the second step may involve obtaining a second thermal gradient formula by measuring an internal temperature at different locations along the thickness direction of the test piece of the metal layer.

In the general aspect, an internal temperature along the thickness direction of the test piece of the metal base or the test piece of the coating layer may be determined by the Formula:

$$T=aX+b$$

(T: a temperature along the thickness direction of the test piece of the metal base or the test piece of the coating layer, X: coordinates along the thickness direction of the test piece of the metal base or the test piece of the coating layer)

According to an example of a method of testing the insulation performance of a heat shield coating layer, it is possible to maximize the convenience of manufacturing a test piece by using a coin-shaped test piece.

Furthermore, according to this example, it is possible to improve the precision and the reliability of evaluating the heat shield performance because the performance of a heat-shielding coating layer is measured in exposure to a high temperature environment and a cooling fluid that are similar to the actual condition, and the evaluation takes into account the shape of the boundary of the coating layer and the base metal, as well as the effect of adhesives to the coating layer.

According to another example, there is provided an apparatus for evaluating thermal performance of a coating layer, the apparatus including: a first thermal gradient determiner configured to determine a first thermal gradient of a metal-base test piece in response to receiving a temperature measurement taken while one side of the metal-base test piece is exposed to heat and another side of the metal-base test piece is exposed to a cooling air; a second thermal gradient determiner configured to determine a second thermal gradient of a coating-layer test piece in response to receiving a temperature measurement taken while a coating layer side of the coating-layer test piece is exposed to heat and an opposite side of the coating layer test piece is exposed to a cooling air; and a calculator configured to calculate an exterior temperature $T_f$ of a coating layer in the coating layer test piece and a temperature $T_e$ of a boundary side of the coating layer using the first thermal gradient.

The calculator may be configured to calculate a temperature difference $T_\Delta$ between the exterior temperature $T_f$ of the coating layer and the temperature $T_e$ of the boundary side of the coating layer. The apparatus may be configured to evaluate thermal performance of the coating layer using the calculated temperature difference $T_\Delta$ between the exterior temperature $T_f$ of the coating layer and the temperature $T_e$ of the boundary side of the coating layer. The apparatus may further include a temperature measuring device configured to measure a temperature on surfaces of the metal base test piece and the coating layer test piece. The first thermal gradient determiner, second thermal gradient determiner and the calculator may be implemented as one or more processor of a computer or a computing device.

INDUSTRIAL FEASIBILITY

Provided herein is a method for testing the thermal performance of a heat shield coating layer by calculating a temperature difference between both sides of the coating layer based on a temperature gradient of a test piece of a metal base, convective heat transfer coefficient of a high temperature electrical furnace and cooling air, and a temperature gradient of the test piece of the coating layer.

The steps of a method for testing the thermal performance of a heat shield coating layer according to the present disclosure may be performed by a computer or a computing device. Various calculations described above may be performed by a processor of a computer or a computing device. A processor is a hardware component of a computer or a computing device.

The methods and steps described above may be implemented using one or more hardware components, one or more software components, or a combination of one or more hardware components and one or more software components. A hardware component may be, for example, a physical device that physically performs one or more operations, but is not limited thereto. Examples of hardware components include analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The media may also include, alone or in combination with the software program instructions, data files, data structures, and the like. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method for testing thermal performance of a coating layer, the method comprising:
    obtaining a first thermal gradient by exposing one side of a metal base test piece to heat and exposing another side of the metal base test piece to a cooling air;
    obtaining a second thermal gradient by exposing a coating layer side of a coating layer test piece to heat and exposing an opposite side to a cooling air, the second thermal gradient being used to calculate a surface temperature of both sides of the metal base test piece;
    calculating an exterior temperature $T_f$ of a coating layer of the coating layer test piece and a temperature $T_e$ of a boundary side of the coating layer using the first thermal gradient; and
    testing thermal performance of the coating layer by calculating a temperature difference $T_A$ between the exterior temperature $T_f$ of the coating layer and the temperature $T_e$ of the boundary side of the coating layer, wherein a higher value of the calculated temperature difference indicates a higher thermal performance of the coating layer.

2. The method according to claim 1, further comprising:
    in response to obtaining of the first thermal gradient, performing a first surface temperature calculating step of calculating a surface temperature of both sides of the metal base test piece using the obtained first thermal gradient, and performing a convective heat transfer coefficient calculating step of calculating a convective heat transfer coefficient of an interior of a furnace producing the heat and the cooling air using surface temperatures of both sides of the test piece of the metal base, and performing a second surface temperature calculating step of calculating a surface temperature of both sides of the test piece of the metal layer using the obtained second thermal gradient; and
    wherein the calculating of the exterior temperature $T_f$ comprises calculating the exterior temperature $T_f$ of the coating layer and the calculating of the temperature $T_e$ of the boundary side of the coating layer comprises using the convective heat transfer coefficient and the surface temperatures of both sides of a metal layer of the coating layer test piece or the metal base test piece.

3. The method according to claim 1,
    wherein the obtaining of the first thermal gradient comprises measuring an internal temperature at different locations along a thickness direction of the metal base test piece, and
    the obtaining of the second thermal gradient comprises measuring an internal temperature at different locations along a thickness direction of a metal layer of the coating layer test piece.

4. The method according to claim 2,
    wherein the obtaining of the first thermal gradient comprises measuring an internal temperature at different locations along a thickness direction of the metal base test piece, and
    the obtaining of the second thermal gradient comprises measuring an internal temperature at different locations along a thickness direction of a metal layer of the coating layer test piece.

5. The method according to claim 2, wherein the first thermal gradient or the second thermal gradient representing an internal temperature along a thickness direction of the metal base test piece or the coating layer test piece is determined by using the following formula:

$$T = aX + b,$$

wherein T represents a temperature along the thickness direction of the metal base test piece or the coating layer test piece;
X represents coordinates along the thickness direction of the metal base test piece or the coating layer test piece; and
a and b each represent a numerical value.

6. The method according to claim 3,
    wherein the first temperature gradient or the second temperature gradient representing an internal temperature along a thickness direction of the metal base test piece or the coating layer test piece is determined by using the following formula:

$$T = aX + b,$$

wherein T represents a temperature along the thickness direction of the metal base test piece or the coating layer test piece;
X represents coordinates along the thickness direction of the metal base test piece or the coating layer test piece; and
a and b each represent a numerical value.

7. The method of claim 1, wherein the metal base test piece comprises a metal base having a shape of a coin, and the coating layer test piece comprises a second metal base having a shape of a coin and a ceramic coating layer disposed on one surface of the second metal base.

8. A non-transitory computer readable recording medium storing an instruction that causes a computer to perform the method of claim 1.

9. An apparatus for evaluating thermal performance of a coating layer, the apparatus comprising:
    a metal-base test piece comprising a comprising a metal having a shape of a coin a coating layer test piece comprising a second metal base having a ceramic coating layer;
    a processor configured to, using a temperature measuring device:
    determine a first thermal gradient of the metal-base test piece in response to receiving a temperature measurement taken while one side of the metal-base test piece is exposed to heat and another side of the metal-base test piece is exposed to a cooling air;

determine a second thermal gradient of a coating-layer test piece in response to receiving a temperature measurement taken while the coating layer side of the coating-layer test piece is exposed to heat and an opposite side of the coating layer test piece is exposed to a cooling air, the second thermal gradient used to calculate a surface temperature of both side of the metal base test piece;

calculate an exterior temperature $T_f$ of a coating layer in the coating layer test piece and a temperature $T_e$ of a boundary side of the coating layer using the first thermal gradient; and evaluate the thermal performance of the coating layer based on a temperature difference between the exterior temperature $T_f$ of the coating layer and the temperature $T_e$ of the boundary side of the coating layer, wherein a higher value of the calculated temperature difference indicates a higher thermal performance of the coating layer.

10. The apparatus of claim 9, wherein the temperature measuring device is inserted into a first hole and a second hole of the metal base test piece and the coating layer test piece and configured to measure a temperature on surfaces of the metal base test piece and the coating layer test piece.

* * * * *